(12) United States Patent
Baichwal et al.

(10) Patent No.: US 6,211,337 B1
(45) Date of Patent: Apr. 3, 2001

(54) RIP: NOVEL HUMAN PROTEIN INVOLVED IN TUMOR NECROSIS FACTOR SIGNAL TRANSDUCTION

(75) Inventors: Vijay R. Baichwal, San Mateo; Jianing Huang, San Bruno; Hailing Hsu, Moon Park; David V. Goeddel, Hillsborough, all of CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/132,118

(22) Filed: Aug. 11, 1998

Related U.S. Application Data

(63) Continuation-in-part of application No. 08/553,727, filed on Oct. 23, 1995, now abandoned.

(51) Int. Cl.[7] .................................................. C07K 14/435
(52) U.S. Cl. ........................... 530/350; 435/194; 436/501
(58) Field of Search ..................................... 530/351, 350, 530/395; 425/85.7; 514/2, 8; 435/194; 436/501

(56) References Cited

U.S. PATENT DOCUMENTS 5,674,734 * 10/1997 Leder et al. ...................... 435/252.3

* cited by examiner

*Primary Examiner*—Lorraine Spector
*Assistant Examiner*—Eliane Lazar-Wesley
(74) *Attorney, Agent, or Firm*—Richard Aron Osman

(57) ABSTRACT

The invention relates to a human Receptor Interacting Protein (hRIP), nucleic acids which encode hRIP and methods of using the subject compositions; in particular, methods such as hRIP-based in vitro binding assays and phosphorylation assays for screening chemical libraries for lead compounds for pharmacological agents.

24 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2016 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..2013

(xi) SEQUENCE DESCRIPTION: SEQ ID NO:1:

```
ATG CAA CCA GAC ATG TCC TTG AAT GTC ATT AAG ATG AAA TCC AGT GAC        48
Met Gln Pro Asp Met Ser Leu Asn Val Ile Lys Met Lys Ser Ser Asp
 1               5                  10                  15

TTC CTG GAG AGT GCA GAA CTG GAC AGC GGA GGC TTT GGG AAG GTG TCT        96
Phe Leu Glu Ser Ala Glu Leu Asp Ser Gly Gly Phe Gly Lys Val Ser
                20                  25                  30

CTG TGT TTC CAC AGA ACC CAG GGA CTC ATG ATC ATG AAA ACA GTG TAC       144
Leu Cys Phe His Arg Thr Gln Gly Leu Met Ile Met Lys Thr Val Tyr
            35                  40                  45

AAG GGG CCC AAC TGC ATT GAG CAC AAC GAG GCC CTC TTG GAG GAG GCG       192
Lys Gly Pro Asn Cys Ile Glu His Asn Glu Ala Leu Leu Glu Glu Ala
        50                  55                  60

AAG ATG ATG AAC AGA CTG AGA CAC AGC CGG GTG GTG AAG CTC CTG GGC       240
Lys Met Met Asn Arg Leu Arg His Ser Arg Val Val Lys Leu Leu Gly
 65                  70                  75                  80
```

```
GTC ATC ATA GAG GAA GGG AAG TAC TCC CTG GTG ATG GAG TAC ATG GAG        288
Val Ile Ile Glu Glu Gly Lys Tyr Ser Leu Val Met Glu Tyr Met Glu
                 85                  90                  95

AAG GGC AAC CTG ATG CAC GTG CTG AAA GCC GAG ATG AGT ACT CCG CTT        336
Lys Gly Asn Leu Met His Val Leu Lys Ala Glu Met Ser Thr Pro Leu
            100                 105                 110

TCT GTA AAA GGA AGG ATA ATT TTG GAA ATC ATT GAA GGA ATG TGC TAC        384
Ser Val Lys Gly Arg Ile Ile Leu Glu Ile Ile Glu Gly Met Cys Tyr
            115                 120                 125

TTA CAT GGA AAA GGC GTG ATA CAC AAG GAC CTG AAG CCT GAA AAT ATC        432
Leu His Gly Lys Gly Val Ile His Lys Asp Leu Lys Pro Glu Asn Ile
        130                 135                 140

CTT GTT GAT AAT GAC TTC CAC ATT AAG ATC GCA GAC CTC GGC CTT GCC        480
Leu Val Asp Asn Asp Phe His Ile Lys Ile Ala Asp Leu Gly Leu Ala
145                 150                 155                 160

TCC TTT AAG ATG TGG AGC AAA CTG AAT AAT GAA GAG CAC AAT GAG CTG        528
Ser Phe Lys Met Trp Ser Lys Leu Asn Asn Glu Glu His Asn Glu Leu
                165                 170                 175

AGG GAA GTG GAC GGC ACC GCT AAG AAG AAT GGC GGC ACC CTC TAC TAC        576
Arg Glu Val Asp Gly Thr Ala Lys Lys Asn Gly Gly Thr Leu Tyr Tyr
            180                 185                 190

ATG GCG CCC GAG CAC CTG AAT GAC GTC AAC GCA AAG CCC ACA GAG AAG        624
Met Ala Pro Glu His Leu Asn Asp Val Asn Ala Lys Pro Thr Glu Lys
            195                 200                 205

TCG GAT GTG TAC AGC TTT GCT GTA GTA CTC TGG GCG ATA TTT GCA AAT        672
Ser Asp Val Tyr Ser Phe Ala Val Val Leu Trp Ala Ile Phe Ala Asn
210                 215                 220

AAG GAG CCA TAT GAA AAT GCT ATC TGT GAG CAG CAG TTG ATA ATG TGC        720
Lys Glu Pro Tyr Glu Asn Ala Ile Cys Glu Gln Gln Leu Ile Met Cys
225                 230                 235                 240

ATA AAA TCT GGG AAC AGG CCA GAT GTG GAT GAC ATC ACT GAG TAC TGC        768
Ile Lys Ser Gly Asn Arg Pro Asp Val Asp Asp Ile Thr Glu Tyr Cys
                245                 250                 255

CCA AGA GAA ATT ATC AGT CTC ATG AAG CTC TGC TGG GAA GCG AAT CCG        816
Pro Arg Glu Ile Ile Ser Leu Met Lys Leu Cys Trp Glu Ala Asn Pro
            260                 265                 270

GAA GCT CGG CCG ACA TTT CCT GGC ATT GAA GAA AAA TTT AGG CCT TTT        864
Glu Ala Arg Pro Thr Phe Pro Gly Ile Glu Glu Lys Phe Arg Pro Phe
            275                 280                 285

TAT TTA AGT CAA TTA GAA GAA AGT GTA GAA GAG GAC GTG AAG AGT TTA        912
Tyr Leu Ser Gln Leu Glu Glu Ser Val Glu Glu Asp Val Lys Ser Leu
290                 295                 300

AAG AAA GAG TAT TCA AAC GAA AAT GCA GTT GTG AAG AGA ATG CAG TCT        960
Lys Lys Glu Tyr Ser Asn Glu Asn Ala Val Val Lys Arg Met Gln Ser
305                 310                 315                 320

CTT CAA CTT GAT TGT GTG GCA GTA CCT TCA AGC CGG TCA AAT TCA GCC       1008
Leu Gln Leu Asp Cys Val Ala Val Pro Ser Ser Arg Ser Asn Ser Ala
                325                 330                 335

ACA GAA CAG CCT GGT TCA CTG CAC AGT TCC CAG GGA CTT GGG ATG GGT       1056
Thr Glu Gln Pro Gly Ser Leu His Ser Ser Gln Gly Leu Gly Met Gly
            340                 345                 350

CCT GTG GAG GAG TCC TGG TTT GCT CCT TCC CTG GAG CAC CCA CAA GAA       1104
Pro Val Glu Glu Ser Trp Phe Ala Pro Ser Leu Glu His Pro Gln Glu
            355                 360                 365

GAG AAT GAG CCC AGC CTG CAG AGT AAA CTC CAA GAC GAA GCC AAC TAC       1152
Glu Asn Glu Pro Ser Leu Gln Ser Lys Leu Gln Asp Glu Ala Asn Tyr
        370                 375                 380

CAT CTT TAT GGC AGC CGC ATG GAC AGG CAG ACG AAA CAG CAG CCC AGA       1200
His Leu Tyr Gly Ser Arg Met Asp Arg Gln Thr Lys Gln Gln Pro Arg
385                 390                 395                 400
```

```
CAG AAT GTG GCT TAC AAC AGA GAG GAG GAA AGG AGA CGC AGG GTC TCC        1248
Gln Asn Val Ala Tyr Asn Arg Glu Glu Glu Arg Arg Arg Arg Val Ser
                405                 410                 415

CAT GAC CCT TTT GCA CAG CAA AGA CCT TAC GAG AAT TTT CAG AAT ACA        1296
His Asp Pro Phe Ala Gln Gln Arg Pro Tyr Glu Asn Phe Gln Asn Thr
            420                 425                 430

GAG GGA AAA GGC ACT GTT TAT TCC AGT GCA GCC AGT CAT GGT AAT GCA        1344
Glu Gly Lys Gly Thr Val Tyr Ser Ser Ala Ala Ser His Gly Asn Ala
        435                 440                 445

GTG CAC CAG CCC TCA GGG CTC ACC AGC CAA CCT CAA GTA CTG TAT CAG        1392
Val His Gln Pro Ser Gly Leu Thr Ser Gln Pro Gln Val Leu Tyr Gln
    450                 455                 460

AAC AAT GGA TTA TAT AGC TCA CAT GGC TTT GGA ACA AGA CCA CTG GAT        1440
Asn Asn Gly Leu Tyr Ser Ser His Gly Phe Gly Thr Arg Pro Leu Asp
465                 470                 475                 480

CCA GGA ACA GCA GGT CCC AGA GTT TGG TAC AGG CCA ATT CCA AGT CAT        1488
Pro Gly Thr Ala Gly Pro Arg Val Trp Tyr Arg Pro Ile Pro Ser His
                485                 490                 495

ATG CCT AGT CTG CAT AAT ATC CCA GTG CCT GAG ACC AAC TAT CTA GGA        1536
Met Pro Ser Leu His Asn Ile Pro Val Pro Glu Thr Asn Tyr Leu Gly
            500                 505                 510

AAT ACA CCC ACC ATG CCA TTC AGC TCC TTG CCA CCA ACA GAT GAA TCT        1584
Asn Thr Pro Thr Met Pro Phe Ser Ser Leu Pro Pro Thr Asp Glu Ser
        515                 520                 525

ATA AAA TAT ACC ATA TAC AAT AGT ACT GGC ATT CAG ATT GGA GCC TAC        1632
Ile Lys Tyr Thr Ile Tyr Asn Ser Thr Gly Ile Gln Ile Gly Ala Tyr
    530                 535                 540

AAT TAT ATG GAG ATT GGT GGG ACG AGT TCA TCA CTA CTA GAC AGC ACA        1680
Asn Tyr Met Glu Ile Gly Gly Thr Ser Ser Ser Leu Leu Asp Ser Thr
545                 550                 555                 560

AAT ACG AAC TTC AAA GAA GAG CCA GCT GCT AAG TAC CAA GCT ATC TTT        1728
Asn Thr Asn Phe Lys Glu Glu Pro Ala Ala Lys Tyr Gln Ala Ile Phe
                565                 570                 575

GAT AAT ACC ACT AGT CTG ACG GAT AAA CAC CTG GAC CCA ATC AGG GAA        1776
Asp Asn Thr Thr Ser Leu Thr Asp Lys His Leu Asp Pro Ile Arg Glu
            580                 585                 590

AAT CTG GGA AAG CAC TGG AAA AAC TGT GCC CGT AAA CTG GGC TTC ACA        1824
Asn Leu Gly Lys His Trp Lys Asn Cys Ala Arg Lys Leu Gly Phe Thr
        595                 600                 605

CAG TCT CAG ATT GAT GAA ATT GAC CAT GAC TAT GAG CGA GAT GGA CTG        1872
Gln Ser Gln Ile Asp Glu Ile Asp His Asp Tyr Glu Arg Asp Gly Leu
    610                 615                 620

AAA GAA AAG GTT TAC CAG ATG CTC CAA AAG TGG GTG ATG AGG GAA GGC        1920
Lys Glu Lys Val Tyr Gln Met Leu Gln Lys Trp Val Met Arg Glu Gly
625                 630                 635                 640

ATA AAG GGA GCC ACG GTG GGG AAG CTG GCC CAG GCG CTC CAC CAG TGT        1968
Ile Lys Gly Ala Thr Val Gly Lys Leu Ala Gln Ala Leu His Gln Cys
                645                 650                 655

TCC AGG ATC GAC CTT CTG AGC AGC TTG ATT TAC GTC AGC CAG AAC            2013
Ser Arg Ile Asp Leu Leu Ser Ser Leu Ile Tyr Val Ser Gln Asn
            660                 665                 670

TAA                                                                    2016

(2) INFORMATION FOR SEQ ID NO:2:

(i) SEQUENCE CHARACTERISTICS:
        (A) LENGTH: 671 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Gln Pro Asp Met Ser Leu Asn Val Ile Lys Met Lys Ser Ser Asp
 1               5                  10                  15

Phe Leu Glu Ser Ala Glu Leu Asp Ser Gly Gly Phe Gly Lys Val Ser
            20                  25                  30

Leu Cys Phe His Arg Thr Gln Gly Leu Met Ile Met Lys Thr Val Tyr
        35                  40                  45

Lys Gly Pro Asn Cys Ile Glu His Asn Glu Ala Leu Leu Glu Glu Ala
    50                  55                  60

Lys Met Met Asn Arg Leu Arg His Ser Arg Val Val Lys Leu Leu Gly
65                  70                  75                  80

Val Ile Ile Glu Glu Gly Lys Tyr Ser Leu Val Met Glu Tyr Met Glu
                85                  90                  95

Lys Gly Asn Leu Met His Val Leu Lys Ala Glu Met Ser Thr Pro Leu
            100                 105                 110

Ser Val Lys Gly Arg Ile Ile Leu Glu Ile Ile Glu Gly Met Cys Tyr
        115                 120                 125

Leu His Gly Lys Gly Val Ile His Lys Asp Leu Lys Pro Glu Asn Ile
    130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
        195                 200                 205

Ser Asp Val Tyr Ser Phe Ala Val Val Leu Trp Ala Ile Phe Ala Asn
    210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270

Glu Ala Arg Pro Thr Phe Pro Gly Ile Glu Glu Lys Phe Arg Pro Phe
        275                 280                 285

Tyr Leu Ser Gln Leu Glu Glu Ser Val Glu Glu Asp Val Lys Ser Leu
    290                 295                 300

Lys Lys Glu Tyr Ser Asn Glu Asn Ala Val Val Lys Arg Met Gln Ser
305                 310                 315                 320

Leu Gln Leu Asp Cys Val Ala Val Pro Ser Ser Arg Ser Asn Ser Ala
                325                 330                 335

Thr Glu Gln Pro Gly Ser Leu His Ser Ser Gln Gly Leu Gly Met Gly
            340                 345                 350

Pro Val Glu Glu Ser Trp Phe Ala Pro Ser Leu Glu His Pro Gln Glu
        355                 360                 365

Glu Asn Glu Pro Ser Leu Gln Ser Lys Leu Gln Asp Glu Ala Asn Tyr
    370                 375                 380

His Leu Tyr Gly Ser Arg Met Asp Arg Gln Thr Lys Gln Gln Pro Arg
385                 390                 395                 400
```

-continued

```
Gln Asn Val Ala Tyr Asn Arg Glu Glu Arg Arg Arg Val Ser
            405                 410                 415

His Asp Pro Phe Ala Gln Gln Arg Pro Tyr Glu Asn Phe Gln Asn Thr
                420             425                 430

Glu Gly Lys Gly Thr Val Tyr Ser Ser Ala Ala Ser His Gly Asn Ala
        435                 440                 445

Val His Gln Pro Ser Gly Leu Thr Ser Gln Pro Gln Val Leu Tyr Gln
    450                 455                 460

Asn Asn Gly Leu Tyr Ser Ser His Gly Phe Gly Thr Arg Pro Leu Asp
465                 470                 475                 480

Pro Gly Thr Ala Gly Pro Arg Val Trp Tyr Arg Pro Ile Pro Ser His
            485                 490                 495

Met Pro Ser Leu His Asn Ile Pro Val Pro Glu Thr Asn Tyr Leu Gly
                500                 505                 510

Asn Thr Pro Thr Met Pro Phe Ser Ser Leu Pro Pro Thr Asp Glu Ser
            515                 520                 525

Ile Lys Tyr Thr Ile Tyr Asn Ser Thr Gly Ile Gln Ile Gly Ala Tyr
        530                 535                 540

Asn Tyr Met Glu Ile Gly Gly Thr Ser Ser Ser Leu Leu Asp Ser Thr
545                 550                 555                 560

Asn Thr Asn Phe Lys Glu Glu Pro Ala Ala Lys Tyr Gln Ala Ile Phe
                565                 570                 575

Asp Asn Thr Thr Ser Leu Thr Asp Lys His Leu Asp Pro Ile Arg Glu
            580                 585                 590

Asn Leu Gly Lys His Trp Lys Asn Cys Ala Arg Lys Leu Gly Phe Thr
        595                 600                 605

Gln Ser Gln Ile Asp Glu Ile Asp His Asp Tyr Glu Arg Asp Gly Leu
    610                 615                 620

Lys Glu Lys Val Tyr Gln Met Leu Gln Lys Trp Val Met Arg Glu Gly
625                 630                 635                 640

Ile Lys Gly Ala Thr Val Gly Lys Leu Ala Gln Ala Leu His Gln Cys
                645                 650                 655

Ser Arg Ile Asp Leu Leu Ser Ser Leu Ile Tyr Val Ser Gln Asn
            660                 665                 670
```

RIP: NOVEL HUMAN PROTEIN INVOLVED IN TUMOR NECROSIS FACTOR SIGNAL TRANSDUCTION

CROSS-REFERENCE TO RELATED APPLICATION

This is a CIP of claims priority under 35USC120 to U.S. patent application Ser. No. 08/553,727, filed Oct. 23, 1995 now abandoned.

INTRODUCTION

1. Field of the Invention

The field of this invention is a novel human kinase involved in tumor necrosis factor signal transduction and its use in drug screening.

2. Background

Tumor necrosis factor (TNF) is an important cytokine involved in the signaling of a number of cellular responses including cytotoxicity, anti-viral activity, immun.-regulatory activities and the transcriptional regulation of a number of genes. The TNF receptors (TNF-R1 and TNF-R2) are members of the larger TNF receptor superfamily which also includes the Fas antigen, CD27, CD30, CD40, and the low affinity nerve growth factor receptor. Members of this family have been shown to participate in a variety of biological properties, including programmed cell death, antiviral activity and activation of the transcription factor NF-κB in a wide variety of cell types.

Accordingly, it is desired to identify agents which specifically modulate transduction of TNF receptor family signaling. Unfortunately, the components of the signaling pathway remain largely unknown; hence, the reagents necessary for the development of high-throughput screening assays for such therapeutics are unavailable. Elucidation of TNF receptor family signal transduction pathways leading to NF-κB activation would provide valuable insight into mechanisms to alleviate inflammation. In particular, components of this pathway would provide valuable targets for automated, cost-effective, high throughput drug screening and hence would have immediate application in a broad range of domestic and international pharmaceutical and biotechnology drug development programs.

Relevant Literature

Stanger et al. (1995) Cell 81, 513–523 report the existence of a Receptor Interacting Protein (RIP) and its functional expression. VanArsdale and Ware (1994) J Immunology 153:3043–3050 describe proteins associated with TNF-R1. The cloning and amino acid sequencing of TNF-R1 is disclosed in Schall et al (1990) Cell 61, 361 and Loetscher et al (1990) Cell 61, 351; the identification of a "death domain" in TNF-R1 is disclosed in Tartaglia et al. (1993) Cell 74:845–853. The cloning and amino acid sequence of a TNF-R associated death domain protein (TRADD) is described by Hsu et al. (1995) Cell 81, 495–504. The cloning and amino acid sequence of the Fas antigen is disclosed in Itoh et al (1991) Cell 66, 233–243. For a recent review, see Smith et al. (1994) Cell 76:959–962 and Vandenabelle et al. (1995) Trends Cell Biol. 5, 392–399.

SUMMARY OF THE INVENTION

The invention provides methods and compositions relating to a human Receptor Interacting Protein (hRIP). The compositions include nucleic acids which encode hRIP, hRIP kinase domains, and recombinant proteins made from these nucleic acids. The invention also provides methods for screening chemical libraries for lead compounds for a pharmacological agent useful in the diagnosis or treatment of disease associated hRIP activity or hRIP-dependent signal transduction. In one embodiment, the methods involve incubating a mixture of hRIP, a natural intracellular hRIP substrate or binding target and a candidate pharmacological agent and determining if the presence of the agent modulates the ability of hRIP to selectively phosphorylate the substrate or bind the binding target. Specific agents provide lead compounds for pharmacological agents capable of disrupting hRIP function.

DETAILED DESCRIPTION OF THE INVENTION

A human RIP-encoding nucleic acid sequence is set out in SEQ ID NO: 1. A human RIP kinase domain-encoding nucleic acid sequence is set out in SEQ ID NO: 1, nucleotides 1–900. A human RIP amino acid sequence is set out in SEQ ID NO: 2; and a hRIP kinase domain sequence is set out in SEQ ID NO:2, residues 1–300.

Natural nucleic acids encoding hRIP are readily isolated from cDNA libraries with PCR primers and hybridization probes containing portions of the nucleic acid sequence of SEQ ID NO:1. For example, we used low stringency hybridization at 42° C. (hybridization buffer: 20% formamide, 10% Denhardt, 0.5% SDS, 5×SSPE; with membrane washes at room temperature with 5×SSPE/0.5% SDS) with a 120 base oligonucleotide probe (SEQ ID NO: 1, nucleotides 1728–1847) to isolate a native human RIP cDNA from a library prepared from human umbilical vein endothelial cells. In addition, synthetic hRIP-encoding nucleic acids may be generated by automated synthesis.

The subject nucleic acids are recombinant, meaning they comprise a sequence joined to a nucleotide other than that to which sequence is naturally joined and isolated from a natural environment. The nucleic acids may be part of hRIP-expression vectors and may be incorporated into cells for expression and screening, transgenic animals for functional studies (e.g. the efficacy of candidate drugs for disease associated with expression of a hRIP), etc. These nucleic acids find a wide variety of applications including use as templates for transcription, hybridization probes, PCR primers, therapeutic nucleic acids, etc.; use in detecting the presence of hRIP genes and gene transcripts, in detecting or amplifying nucleic acids encoding additional hRIP homologs and structural analogs, and in gene therapy applications.

In a particular embodiment, the invention provides RIP-$\text{Thr}^{514}$ polypeptides, RIP-$\text{Thr}^{514}$ polypeptide-encoding nucleic acids/polynucleotides, and RIP-$\text{Thr}^{514}$ polypeptide-based methods (below), which RIP-$\text{Thr}^{514}$ polypeptides comprise at least 8, preferably at least 10, more preferably at least 12, more preferably at least 16, most preferably at least 24 consecutive amino acid residues of the amino acid sequence set forth as SEQ ID NO:2, which consecutive amino acid residues comprise the amino acid residue 514 (Thr) of SEQ ID NO:2. Exemplary RIP-$\text{Thr}^{514}$ polypeptides having RIP-$\text{Thr}^{514}$ binding specificity and immunologically distinguishable from RIP-$\text{Ser}^{514}$ are shown in Table I.

TABLE I. Exemplary RIP-$\text{Thr}^{514}$ Polypeptides Having RIP-$\text{Thr}^{514}$ Binding Specificity αΔ1 (SEQ ID NO:2, residues 509–518)
αΔ2 (SEQ ID NO:2, residues 514–521)
αΔ3 (SEQ ID NO:2, residues 506–514)
αΔ4 (SEQ ID NO:2, residues 504–524)
αΔ5 (SEQ ID NO:2, residues 498–514)

αΔ6 (SEQ ID NO:2, residues 514–534)
αΔ7 (SEQ ID NO:2, residues 513–520)
αΔ8 (SEQ ID NO:2, residues 508–515)
αΔ9 (SEQ ID NO:2, residues 512–522)
αΔ10 (SEQ ID NO:2, residues 423–514)
αΔ11 (SEQ ID NO:2, residues 423–543)
αΔ12 (SEQ ID NO:2, residues 423–579)
αΔ13 (SEQ ID NO:2, residues 423–633)
αΔ14 (SEQ ID NO:2, residues 423–671)
αΔ15 (SEQ ID NO:2, residues 514–543)
αΔ16 (SEQ ID NO:2, residues 514–579)
αΔ17 (SEQ ID NO:2, residues 514–633)
αΔ18 (SEQ ID NO:2, residues 514–671)

In a particular embodiment, the invention provides RIP-ACA$^{1540-1542}$ polynucleotides, comprising at least 18, 24, 36, 48, 72, 148, 356 or 728 consecutive nucleotides of the nucleotide sequence set forth as SEQ ID NO:1, which consecutive polynucleotides comprise the polynucleotides 1540–1542 (ACA) of SEQ ID NO:1. Exemplary RIP-ACA$^{1540-1542}$ polynucleotides and allele specific oligonucleotide probes having RIP-ACA$^{1540-1542}$ binding specificity and distinguishable by hybridization assays from RIP-TCT$^{1540-1542}$ are shown in Table II.

TABLE II. Exemplary RIP-ACA$^{1540-1542}$ Polynucleotides Having RIP-ACA$^{1540-1542}$ Binding Specificity αΔ1 (SEQ ID NO:1, nucleotides 1540–1557)
αΔ2 (SEQ ID NO:1, nucleotides 1540–1563)
αΔ3 (SEQ ID NO:1, nucleotides 1540–1675)
αΔ4 (SEQ ID NO:1, nucleotides 1540–1699)
αΔ5 (SEQ ID NO:1, nucleotides 1525–1542)
αΔ6 (SEQ ID NO:1, nucleotides 1519–1542)
αΔ7 (SEQ ID NO:1, nucleotides 1507–1542)
αΔ8 (SEQ ID NO:1, nucleotides 1483–1542)
αΔ9 (SEQ ID NO:1, nucleotides 1537–1545)
αΔ10 (SEQ ID NO:1, nucleotides 1534–1548)
αΔ11 (SEQ ID NO:1, nucleotides 1528–1554)
αΔ12 (SEQ ID NO:1, nucleotides 1516–1566)
αΔ13 (SEQ ID NO:1, nucleotides 1504–1554)
αΔ14 (SEQ ID NO:1, nucleotides 1492–1568)

The invention provides efficient methods of identifying pharmacological agents or lead compounds for agents active at the level of a hRIP modulatable cellular function, particularly hRIP mediated TNF receptor or Tumor necrosis factor receptor associated Factor-2 (TRAF2) or TRADD-induced signal transduction. For example, we have found that a binding complex comprising TNF R1, TRADD, and hRIP exists in TNF-stimulated cells. Generally, the screening methods involve assaying for compounds which interfere with a hRIP activity such as kinase activity or TRAF2 or TRADD binding. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising hRIP and one or more natural hRIP intracellular binding targets including substrates or otherwise modulating hRIP kinase activity. Target indications may include infection, genetic disease, cell growth and regulatory or immunologic dysfunction, such as neoplasia, inflammation, hypersensitivity, etc.

A wide variety of assays for binding agents are provided including labeled in vitro kinase assays, protein-protein binding assays, immunoassays, cell based assays, etc. The hRIP compositions used in the methods are recombinantly produced from nucleic acids having the disclosed hRIP nucleotide sequences. The hRIP may be part of a fusion product with another peptide or polypeptide, e.g. a polypeptide that is capable of providing or enhancing protein-protein binding, stability under assay conditions (e.g. a tag for detection or anchoring), etc.

The assay mixtures comprise one or more natural intracellular hRIP binding targets including substrates, such as TRADD, TRAF2, or, in the case of an autophosphorylation assay, the hRIP itself can function as the binding target. In one embodiment, the mixture comprises a complex of hRIP, TRADD and TNFR1. A hRIP derived pseudosubstrate may be used or modified (e.g. A to S/T substitutions) to generate effective substrates for use in the subject kinase assays as can synthetic peptides or other protein substrates. Generally, hRIP-specificity of the binding agent is shown by kinase activity (i.e. the agent demonstrates activity of an hRIP substrate, agonist, antagonist, etc.) or binding equilibrium constants (usually at least about $10^6$ M$^{-1}$, preferably at least about $10^8$ M$^{-1}$, more preferably at least about $10^9$ M$^{-1}$). A wide variety of cell-based and cell-free assays may be used to demonstrate hRIP-specific binding; preferred are rapid in vitro, cell-free assays such as mediating or inhibiting hRIP-protein (e.g. hRIP-TRADD) binding, phosphorylation assays, immunoassays, etc.

The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

In a preferred in vitro, binding assay, a mixture of at least the kinase domain of hRIP, one or more binding targets or substrates and the candidate agent is incubated under conditions whereby, but for the presence of the candidate pharmacological agent, the hRIP specifically binds the cellular binding target at a first binding affinity or phosphorylates the substrate at a first rate. After incubation, a second binding affinity or rate is detected. Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected.

The following examples are offered by way of illustration and not by way of limitation.

EXAMPLES

1. Protocol for hRIP Autophosphorylation Assay

A. Reagents:

Neutralite Avidin: 20 μg/ml in PBS.
hRIP: $10^{-8}$--$10^{-5}$ M biotinylated hRIP kinase domain, residues 1–300 at 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

[$^{32}$P]γ-ATP 10×stock: 2×10$^{-5}$ M cold ATP with 100 μCi [$^{32}$P]γ-ATP. Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml PBS.

B. Preparation of assay plates:

Coat with 120 μl of stock Neutralite avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl biotinylated hRIP (0.1–10 pmoles/40 ul in assay buffer)

Add 10 μl compound or extract.

Add 10 μl [$^{32}$P]γ-ATP 10×stock.

Shake at 30° C. for 15 minutes.

Incubate additional 45 minutes at 30° C.

Stop the reaction by washing 4 times with 200 μl PBS.

Add 150 μl scintillation cocktail.

Count in Topcount.

D. Controls for all assays (located on each plate):

a. Non-specific binding (no RIP added)

b. cold ATP to achieve 80% inhibition.

2. Protocol for hRIP—Substrate Phosphorylation Assay

A. Reagents:

Neutralite Avidin: 20 μg/ml in PBS.

hRIP: 10$^{-8}$–10$^{-5}$ M hRIP at 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

[$^{32}$P]γ-ATP 10×stock: 2×10$^{-5}$ M cold ATP with 100 μCi [$^{32}$P]γ-ATP. Place in the 4° C. microfridge during screening.

Substrate: 2×10$^{-6}$ M biotinylated synthetic peptide kinase substrate at 20 μg/ml in PBS.

Protease inhibitor cocktail (1000×): 10 mg Trypsin Inhibitor (BMB # 109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml PBS.

B. Preparation of assay plates:

Coat with 120 μl of stock Neutralite avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl hRIP (0.1–10 pmoles/40 ul in assay buffer)

Add 10 μl compound or extract.

Shake at 30° C. for 15 minutes.

Add 10 μl [$^{32}$P]γ-ATP 10×stock.

Add 10 μl substrate.

Shake at 30° C. for 15 minutes.

Incubate additional 45 minutes at 30° C.

Stop the reaction by washing 4 times with 200 μl PBS.

Add 150 μl scintillation cocktail.

Count in Topcount.

D. Controls for all assays (located on each plate):

a. Non-specific binding (no RIP added)

b. cold ATP to achieve 80% inhibition.

3. Protocol for hRIP—TRADD Binding Assay

A. Reagents:

Anti-myc antibody: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P hRIP 10×stock: 10$^{-8}$–10$^{-6}$ M "cold" hRIP (full length) supplemented with 200,000–250,000 cpm of labeled hRIP (HMK-tagged) (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml PBS.

TRADD: 10$^{-8}$–10$^{-5}$ M myc eptitope-tagged TRADD in PBS.

B. Preparation of assay plates:

Coat with 120 μl of stock anti-myc antibody per well overnight at 4° C.

Wash 2× with 200 μl PBS.

Block with 150 μl of blocking buffer.

Wash 2× with 200 μl PBS.

C. Assay:

Add 40 μl assay buffer/well.

Add 10 μl compound or extract.

Add 10 μl $^{33}$P-RIP (20,000–25,000 cpm/0.1–10 pmoles/well=10$^{-9}$–10$^{-7}$ M final concentration).

Shake at 25° C. for 15 minutes.

Incubate additional 45 minutes at 25° C.

Add 40 μl eptitope-tagged TRADD (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):

a. Non-specific binding (no hRIP added)

b. Soluble (non-tagged TRADD) to achieve 80% inhibition.

4. Protocol for hRIP—TRAF2 Binding Assay

A. Reagents:

Anti-myc antibody: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P hRIP 10×stock: $10^{-8}$–$10^{-6}$ M "cold" hRIP kinase domain, residues 1–300, supplemented with 200,000–250,000 cpm of labeled hRIP kinase domain (HMK-tagged) (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml PBS.

TRAF2: $10^{-8}$–$10^{-5}$ M myc eptitope-tagged TRAF2 in PBS.

B. Preparation of assay plates:

Coat with 120 μl of stock anti-myc antibody per well overnight at 4° C.

Wash 2× with 200 μl PBS.

Block with 150 μl of blocking buffer.

Wash 2× with 200 μl PBS.

C. Assay:

Add 40 μl assay buffer/well.

Add 10 μl compound or extract.

Add 10 μl $^{33}$P-RIP kinase domain (20,000–25,000 cpm/ 0.1–10 pmoles/well=$10^{-9}$–$10^{-7}$ M final concentration).

Shake at 25° C. for 15 minutes.

Incubate additional 45 minutes at 25° C.

Add 40 μl eptitope-tagged TRAF2 (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):

a. Non-specific binding (no hRIP kinase domain added)

b. Soluble (non-tagged TRAF2) to achieve 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated RIP-Thr$^{514}$ polypeptide, comprising at least 10 consecutive amino acid residues of the amino acid sequence set forth as SEQ ID NO:2, which consecutive amino acid residues comprise the amino acid residue 514 (Thr) of SEQ ID NO:2.

2. An isolated polypeptide according to claim 1, wherein said polypeptide has an activity selected from at least one of: a kinase or kinase inhibitory activity or a RIP-binding or binding inhibitory activity.

3. A method of screening for an agent which modulates the interaction of a RIP polypeptide to a binding target, said method comprising the steps of:
   incubating a mixture comprising:
      an isolated polypeptide according to claim 1,
      a binding target of said polypeptide, and
      a candidate agent;
   under conditions whereby, but for the presence of said agent, said polypeptide specifically binds said binding target at a reference affinity;
   detecting the binding affinity of said polypeptide to said binding target to determine an agent-biased affinity, wherein a difference between the agent-biased affinity and the reference affinity indicates that said agent modulates the binding of said polypeptide to said binding target.

4. A method according to claim 3, wherein said binding target is a natural intracellular substrate of the polypeptide and said agent-biased binding affinity is detected as phosphorylation of said substrate.

5. A method according to claim 3, wherein said binding target comprises a Tumor necrosis factor receptor Associated Factor-2 (TRAF2) or a Tumor necrosis factor Receptor-1 Associated Death Domain protein (TRADD).

6. An isolated polypeptide according to claim 1, wherein said consecutive amino acid residues comprise αΔ1 (SEQ ID NO:2, residues 509–518).

7. An isolated polypeptide according to claim 1, wherein said consecutive amino acid residues comprise αΔ2 (SEQ ID NO:2, residues 514–521).

8. An isolated polypeptide according to claim 1, wherein said consecutive amino acid residues comprise αΔ3 (SEQ ID NO:2, residues 506–514).

9. An isolated polypeptide according to claim 1, wherein said consecutive amino acid residues comprise αΔ4 (SEQ ID NO:2, residues 504–524).

10. An isolated polypeptide according to claim 1, wherein said consecutive amino acid residues comprise αΔ5 (SEQ ID NO:2, residues 498–514).

11. An isolated polypeptide according to claim 1, wherein said consecutive amino acid residues comprise αΔ6 (SEQ ID NO:2, residues 514–534).

12. An isolated polypeptide according to claim 1, wherein said consecutive amino acid residues comprise αΔ7 (SEQ ID NO:2, residues 513–520).

13. An isolated polypeptide according to claim 1, wherein said consecutive amino acid residues comprise αΔ8 (SEQ ID NO:2, residues 508–515).

14. An isolated polypeptide according to claim 1, wherein said consecutive amino acid residues comprise αΔ9 (SEQ ID NO:2, residues 512–522).

15. An isolated polypeptide according to claim 1, wherein said consecutive amino acid residues comprise αΔ10 (SEQ ID NO:2, residues 423–514).

16. An isolated polypeptide according to claim 1, wherein said consecutive amino acid residues comprise αΔ11 (SEQ ID NO:2, residues 423–543).

17. An isolated polypeptide according to claim 1, wherein said consecutive amino acid residues comprise αΔ12 (SEQ ID NO:2, residues 423–579).

18. An isolated polypeptide according to claim 1, wherein said consecutive amino acid residues comprise αΔ13 (SEQ ID NO:2, residues 423–633).

19. An isolated polypeptide according to claim 1, wherein said consecutive amino acid residues comprise αΔ14 (SEQ ID NO:2, residues 423–671).

20. An isolated polypeptide according to claim 1, wherein said consecutive amino acid residues comprise αΔ15 (SEQ ID NO:2, residues 514–543).

21. An isolated polypeptide according to claim 1, wherein said consecutive amino acid residues comprise αΔ16 (SEQ ID NO:2, residues 514–579).

22. An isolated polypeptide according to claim 1, wherein said consecutive amino acid residues comprise αΔ17 (SEQ ID NO:2, residues 514–633).

23. An isolated polypeptide according to claim 1, wherein said consecutive amino acid residues comprise αΔ18 (SEQ ID NO:2, residues 514–671).

24. An isolated polypeptide according to claim 1, wherein said consecutive amino acid residues comprise SEQ ID NO:2.

* * * * *